(12) United States Patent
Shen

(10) Patent No.: US 9,259,498 B2
(45) Date of Patent: Feb. 16, 2016

(54) AIR TREATMENT DEVICE

(75) Inventor: Fangzhong Shen, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 101 days.

(21) Appl. No.: 14/232,739

(22) PCT Filed: Jul. 13, 2012

(86) PCT No.: PCT/IB2012/053591
§ 371 (c)(1),
(2), (4) Date: Feb. 18, 2014

(87) PCT Pub. No.: WO2013/011435
PCT Pub. Date: Jan. 24, 2013

(65) Prior Publication Data
US 2014/0199206 A1    Jul. 17, 2014

(30) Foreign Application Priority Data

Jul. 18, 2011    (WO) ................ PCT/CN2011/077272

(51) Int. Cl.
*A61L 9/00*    (2006.01)
*A61L 9/12*    (2006.01)
(Continued)

(52) U.S. Cl.
CPC . *A61L 9/12* (2013.01); *A61L 9/122* (2013.01); *B60H 3/0035* (2013.01); *B60H 3/06* (2013.01); *F24F 3/12* (2013.01); *F24F 11/0079* (2013.01);
(Continued)

(58) Field of Classification Search
CPC ............. A61L 9/00; A61L 9/03; A61L 9/032; A61L 9/122

USPC .......................................... 422/1, 5, 124, 306
See application file for complete search history.

(56) References Cited

U.S. PATENT DOCUMENTS 5,192,342 A    3/1993    Baron
7,776,276 B1    8/2010    Newbolt
(Continued)

FOREIGN PATENT DOCUMENTS

EP    2309198 A1    4/2011
GB    2418142 A    3/2006
(Continued)

*Primary Examiner* — Monzer R Chorbaji

(57) ABSTRACT

An embodiment of the invention provides an air treatment device. The air treatment device comprises an air purifying unit configured to purify air; a scent dispenser configured to dispense scent; an air detector, configured to detect the purified air and provide an output signal; and a processor configured to receive the output signal from the air detector and control the operation speed of the air purifying unit and the dispensing flow of scent dispensed by the scent dispenser, based on the output signal, wherein the dispensing flow of scent dispensed by the scent dispenser is decreased with the increase of the operating speed of the air purifying unit. Another embodiment of the invention provides a method of controlling a scent dispenser and an air purifying unit of an air treatment device, wherein the air treatment device further includes an air detector and a processor. The method comprises the steps of purifying air by using the air purifying unit; detecting the purified air by using the air detector; controlling, by using the processor, the operating speed of the air purifying unit and the dispensing flow of scent dispensed by the scent dispenser, based on the detection result, wherein the dispensing flow of scent dispensed by the scent dispenser is decreased with the increase of the operating speed of the air purifying unit.

9 Claims, 2 Drawing Sheets

(51) Int. Cl.
*F24F 3/12* (2006.01)
*F24F 11/00* (2006.01)
*B60H 3/00* (2006.01)
*B60H 3/06* (2006.01)
*F24F 3/16* (2006.01)

(52) U.S. Cl.
CPC ........ *A61L 2209/11* (2013.01); *A61L 2209/133* (2013.01); *A61L 2209/14* (2013.01); *B60H 2003/0042* (2013.01); *B60H 2003/0683* (2013.01); *F24F 2003/1689* (2013.01); *Y02B 30/746* (2013.01)

(56) References Cited

U.S. PATENT DOCUMENTS

2006/0188238 A1    8/2006  Kent
2008/0193328 A1    8/2008  Crapser
2010/0288847 A1*  11/2010  Gruenbacher et al. .......... 239/34
2011/0033336 A1    2/2011  Kim

FOREIGN PATENT DOCUMENTS

WO    2006023796 A1    3/2006
WO    2009064453 A1    5/2009

* cited by examiner

AIR TREATMENT DEVICE

CROSS-REFERENCE TO PRIOR APPLICATIONS

This application is the U.S. National Phase application under 35 U.S.C. §371 of International Application No. PCT/IB2012/053591, filed on Jul. 13, 2012, which claims the benefit of PCT/CN2011/077272, filed on Jul. 18, 2011. These applications are hereby incorporated by reference herein.

FIELD OF THE INVENTION

The invention relates to the field of air treatment, in particular air treatment devices and methods used in the automotive industry.

BACKGROUND OF THE INVENTION

Urbanization and industrialization cause much air pollution in the megacities, especially those in emerging markets. To purify the ambient air in order to improve air quality, air purifiers are widely used in homes, offices and automobiles to remove, for example, dust, formaldehyde, volatile organic compounds (VOC), germs, etc. Moreover, scent dispensers are also popular; they are used to improve air quality in that they can help remove/conceal/mitigate offensive odors and thus improve people's emotional feelings.

In the existing air purifiers, the scent dispenser is typically integrated with the air purifier to help provide a pleasant smell while purifying air. The air purifier and the scent dispenser mainly operate in the following two ways. In one approach, when the air purifier operates to purify air, the scent dispenser is controlled to open up to dispense scent at a constant speed, i.e. the dispensing flow of scent dispensed by the scent dispenser is kept constant throughout the air purifying process. In the other approach, the dispensing flow of scent dispensed by the scent dispenser is controlled so as to increase with the speed of the fan of the air purifier.

SUMMARY OF THE INVENTION

The inventor of the invention has recognized that when the scent is dispensed by the scent dispenser during the air purifying process, the scent itself will also be absorbed by the filters of the air purifier; the higher the speed of the fan of the air purifier, the more the scent is absorbed by the filters of the air purifier. Consequently, the more the scent is absorbed, the shorter the lifetime of the air purifier. This issue becomes serious when the dispensing flow of scent is kept constant over a long period of time, or even severe when the dispensing flow of scent and the fan speed of the air purifier increase simultaneously.

To better address the above concern, according to one aspect of the invention, an air treatment device is provided. The air treatment device comprises:
    an air purifying unit configured to purify air;
    a scent dispenser configured to dispense scent;
    an air detector configured to detect the purified air and provide an output signal;
    a processor configured to receive the output signal from the air detector and control the operating speed of the air purifying unit and the dispensing flow of scent dispensed by the scent dispenser, based on the output signal, wherein the dispensing flow of scent dispensed by the scent dispenser is decreased with the increase of the operating speed of the air purifying unit.

In a further embodiment, the processor is configured to determine the quality of the purified air based on the output signal, and then control the air purifying unit to purify air at a first speed and control the scent dispenser to dispense a first dispensing flow of scent when the quality of the purified air meets a first criterion, and control the air purifying unit to purify air at a second speed and control the scent dispenser to dispense a second dispensing flow of scent when the quality of the purified air meets a second criterion, wherein the first speed is higher than the second speed and the first dispensing flow of scent is smaller than the second dispensing flow.

The air treatment device enables the dispensing flow of scent and the operating speed of the air purifying unit, i.e. the speed of purifying air, to be controlled by the processor, based on the detected air quality. For example, when the detected quality of the purified air is bad, the air purifying unit is controlled to operate at a higher speed and accordingly the scent dispenser is controlled to dispense a smaller flow of scent. In this manner, the air quality can be improved within a shorter period of time; meanwhile, since less scent is dispensed by the scent dispenser, the total amount of scent absorbed by the filtering unit of the purifying unit will be relatively decreased in this phase. When the detected quality of the purified air is good, the air purifying unit is controlled to operate at a lower speed and accordingly the scent dispenser is controlled to dispense a larger dispensing flow of scent. In this situation, as the air purifying unit purifies air at a lower speed, only a small portion of scent will be absorbed by the filtering unit of the purifying unit in this phase, and in turn a large portion of the scent dispensed by the scent dispenser will be released to the air, which provides a pleasant smell to the user. Meanwhile, since the air purifier works at a lower speed, less scent will be inhaled and absorbed by the filter of the air purifier.

In another aspect of the invention, there is provided a method of controlling a scent dispenser and an air purifying unit of an air treatment device, wherein the air treatment device further includes an air detector and a processor. The method comprises the steps of:
    purifying air by using the air purifying unit;
    detecting the purified air by using the air detector;
    controlling, by using the processor, the operating speed of the air purifying unit and the dispensing flow of the scent dispensed by the scent dispenser, based on the detection result of the air detector, wherein the dispensing flow of scent dispensed by the scent dispenser is decreased with the increase of the operating speed of the air purifying unit.

In one embodiment, the controlling step further comprises:
    determining the quality of the purified air, based on the detection result;
    controlling the air purifying unit to purify air at a first speed and controlling the scent dispenser to dispense a first dispensing flow when the quality of the purified air meets a first criterion; and
    controlling the air purifying unit to purify air at a second speed and controlling the scent dispenser to dispense a second dispensing flow when the quality of the purified air meets a second criterion,
    wherein the first speed is higher than the second speed and the first dispensing flow is lower than the second dispensing flow.

These and other aspects of the invention will be apparent from and elucidated with reference to the embodiments described hereinafter.

DESCRIPTION OF THE DRAWINGS

The above and other objects and features of the present invention will become more apparent from the following detailed description considered in connection with the accompanying drawings, in which.

The same reference numerals are used to denote similar parts throughout the figures.

DETAILED DESCRIPTION

Figure 1:
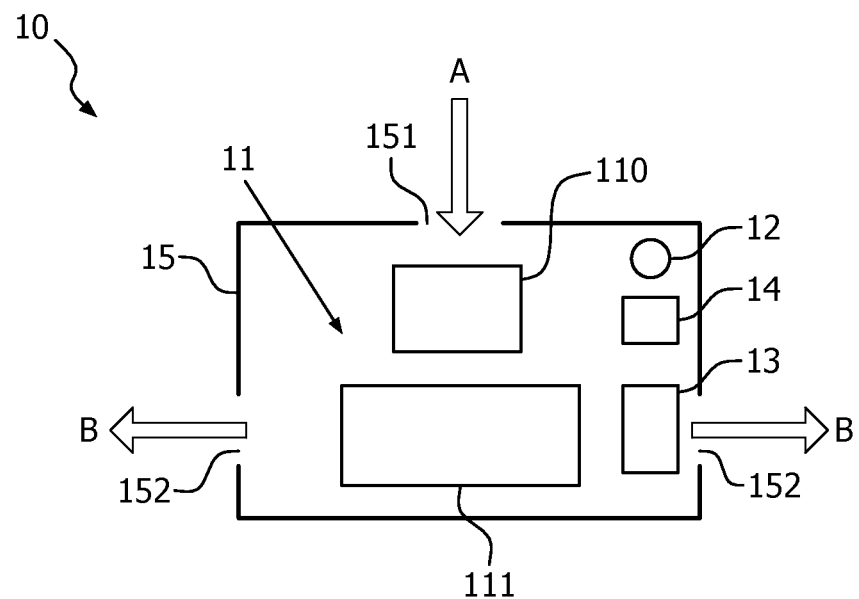
FIG. 1 depicts an exemplary air treatment device according to one aspect of the invention.

FIG. 1 depicts an exemplary air treatment device according to one aspect of the invention. The exemplary air treatment device 10 may generally be used in home, office, automobile or other places of interest, to purify air.

Referring to FIG. 1, the air treatment device 10 comprises an air purifying unit 11 configured to purify air. The air purifying unit 11 may take on various configurations, but it generally includes a filtering unit 110 and an impeller 111. The filtering unit 110 may typically include a particle filter for filtering particles, such as dust from passing air for example, and a gas filter for filtering gases, such as chemical gases from passing air for example. The impeller 111 is configured to force the air to be purified to pass through the filtering unit 110, which may be a backward impeller or a forward impeller for example. In this embodiment, the operating speed of the air purifying unit 11, i.e. the fan speed of the impeller 111, is controllable and adjustable, which may vary in accordance with the quality of the purified air, which will be described in detail later.

The air treatment device 10 further comprises a scent dispenser 12 configured to dispense scent. In this embodiment, the dispensing flow of scent dispensed by the scent dispenser 12 is also controllable and adjustable, which may vary with the quality of the purified air, which will be described in detail later.

The scent dispenser 12 may be of any desired type. For example, referring to FIG. 2, the scent dispenser 12 may include a cartridge 121 containing a fragrant material. An opening 122 is formed in the cartridge 121, allowing the scent generated by the fragrant material to be released there through. The scent dispenser 12 may further include a shield 123 removable disposed on the opening 122 of the cartridge 121. The shield 123 may be coupled to a mini motor 16, for example. In response to a drive signal, the mini motor 16 may drive the shield 123 to move along the longitudinal axis of the cartridge 121 for example, such that the area of the opening 122 exposed to ambient air is adjusted and, in turn, control of the dispensing flow of scent dispensed by the scent dispenser 12 is achieved.

Figure 2:
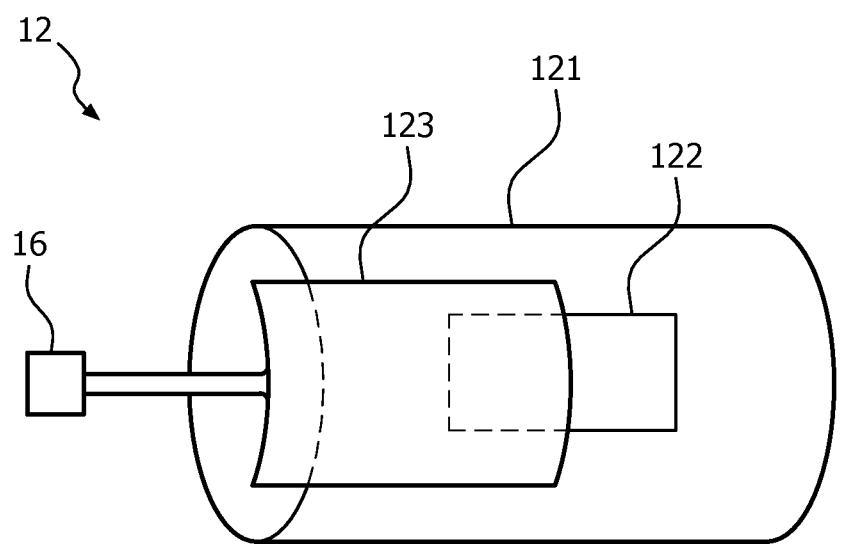
FIG. 2 depicts an exemplary scent dispenser in use together with the air treatment device of FIG. 1.

It will be appreciated that the configuration of the scent dispenser 12 of FIG. 2 is only an illustrative example, and any other scent dispenser capable of achieving the same object may be used instead.

Still referring to FIG. 1, the air treatment device 10 further comprises an air detector 13 configured to detect the quality of the air purified by the air purifying unit 11 and provide an output signal. For example, the air detector 13 may be a particle sensor for detecting the particle level in the purified air and providing an output signal indicative of the particle concentration in the purified air.

The air treatment device 10 further comprises a processor 14 configured to receive the output signal from the air detector 13 and to control the operating speed of the air purifying unit 11 and the dispensing flow of scent dispensed by the scent dispenser 12, based on the output signal. The processor 14 may include any desired type of processing unit, such as a Micro Control Unit (MCU), for example.

The air treatment device 10 may further include a housing 15 for enclosing the air purifying unit 11, the scent dispenser 12, the air detector 13 and the processor 14 described above, which housing may have an inlet 151 and an outlet 152 configured to allow the air to be purified to, respectively, enter (denoted by arrow A) and exit (denoted by arrow B) the air treatment device 10.

To be specific, the processor 14 may be pre-stored with a mapping table which records the mapping relationships between the quality of the purified air and the operating speed of the air purifying unit 11 as well as the flow of scent dispensed by the scent dispenser 12. When the processor 14 receives the output signal from the air detector 13, the processor 14 determines the quality of the purified air, based on the output signal, and then finds, from the mapping table, the desired operating speed of the air purifying unit 11 and the desired flow of scent dispensed by the scent dispenser 12 in dependence on the determined quality of the purified air. Then, the processor 14 controls the air purifying unit 11 to purify air at the desired operating speed and controls the scent dispenser 12 to dispense the desired flow of scent.

In this embodiment, the flow of scent dispensed by the scent dispenser 12 is decreased with the increase of the operating speed of the air purifying unit 11. The reason for this being that when the quality of the purified air is bad, the processor 14 controls the air purifying unit 11 to purify air at a higher speed and controls the scent dispenser 12 to dispense a smaller scent flow. In this manner, the particles distributed in the air can be filtered within a shorter period of time and thus the air quality can be improved rapidly; meanwhile, since the dispensing flow of scent by the scent dispenser 12 is reduced, the total dispensing flow of scent absorbed by the filtering unit 110 will be relatively small in this phase.

When the quality of the purified air becomes good again, the processor 14 controls the air purifying unit 11 to purify air at a lower speed and controls the scent dispenser 12 to dispense a larger dispensing flow of scent. In this situation, as the air purifying unit 11 purifies air at a lower speed, only a small portion of scent dispensed by the scent dispenser 12 will be absorbed by the filtering unit 110 in this phase, but a large portion of the scent dispensed by the scent dispenser 12 will be released into the air, which gives off an odor perceived as pleasant by users.

Table 1 shows an exemplary mapping table pre-stored in the processor 14.

| quality of the purified air | operating speed of the air purifying unit 11 | dispensing flow of scent dispensed by the scent dispenser 12 |
| --- | --- | --- |
| meets a first criterion, for example higher than a first threshold indicative of bad air quality | the first speed | the first dispensing flow |
| meets a second criterion, for example lower than or equal to the first threshold indicative of good air quality | the second speed | the second dispensing flow |

In the exemplary mapping table of table 1, the quality of the purified air is divided into two levels. For the first level (e.g., the particle concentration level of the purified air is higher than the first threshold indicative of bad air quality), the operating speed of the air purifying unit 11 is set to be the first speed, and the dispensing flow of scent dispensed by the scent dispenser 12 is set to be the first dispensing flow; for the second level (i.e. the quality of the purified air is less than or equal to the first threshold indicative of good quality), the operating speed of the air purifying unit 11 is set to be the second speed, and the dispensing flow of scent dispensed by the scent dispenser 12 is set to be the second dispensing flow. In this case, the first speed is higher than the second speed, and the first dispensing flow is smaller than the second dispensing flow.

In one example, the first dispensing flow may be set to zero; that is to say, when the quality of the purified air is bad, the shield 123 is moved to cover the opening 122 of the cartridge 121 completely in such a way that almost no scent is dispensed from the scent dispenser 12.

Table 2 shows another exemplary mapping table pre-stored in the processor 14.

| quality of the purified air | operating speed of the air purifying unit 11 | dispensing flow of scent dispensed by the scent dispenser 12 |
|---|---|---|
| meets a first criterion, for example higher than a first threshold indicative of bad air quality | the first speed | the first dispensing flow |
| meets a second criterion, for example within the range [second threshold, first threshold] indicative of average air quality | the second speed | the second dispensing flow |
| meets a third criterion, for example lower than the second threshold indicative of good air quality | the third speed | the third dispensing flow |

In the exemplary mapping table of table 2, the quality of the purified air is divided into three levels. For the first level (e.g., the particle concentration level of the purified air is higher than the first threshold, indicative of bad air quality), the operating speed of the air purifying unit 11 is set to the first speed, and the dispensing flow of scent dispensed by the scent dispenser 12 is set to the first dispensing flow; for the second level (i.e. the quality of the purified air is within the range [second threshold, first threshold], indicative of average air quality), the operating speed of the air purifying unit 11 is set to the second speed, and the dispensing flow of scent dispensed by the scent dispenser 12 is set to the second dispensing flow; for the third level, (i.e. the quality of the purified air is less than the second threshold, indicative of good air quality), the operating speed of the air purifying unit 11 is set to the third speed, and the dispensing flow of scent dispensed by the scent dispenser 12 is set to the third dispensing flow. Here, the first speed is higher than the second speed, and the second speed is higher than the third speed; the first dispensing flow is smaller than the second dispensing flow, and the second dispensing flow is smaller than the third dispensing flow.

It will be appreciated that the mapping tables shown in table 1 and 2 are only two illustrative examples, and in practical usage, the quality of the purified air may be divided into more than three levels and accordingly the operating speed of the air purifying unit 11 and the dispensing flow of scent dispensed by the scent dispenser 12 may also have more than three levels.

It is to be noted that, in practical usage, for any two adjacent quality levels of the purified air, the dispensing flows of scent dispensed by the scent dispenser 12 may be set to be identical. Likewise, for two adjacent quality levels of the purified air, the operating speeds of the air purifying unit 11 may be set to be identical.

Hereinafter, the operation of the air treatment device 10 will be described by using the mapping table of table 1 as an illustrative example of the mapping table pre-stored in the processor 14.

In operation, once the air treatment device 10, disposed in an automobile for example, is activated, the impeller 111 starts to draw ambient air into the cabin of the automobile, i.e. into the air treatment device 10, via the inlet 151. The ambient air then passes through the filtering unit 110 which filters for example dust and chemical gases from the passing ambient air, and then the purified air exits the air treatment device 10 via the outlet 152 and mixes with the ambient air in the cabin. Meanwhile, the scent dispenser 12 starts to dispense scent. When the air treatment device 10 has just been activated, the air quality in the cabin of the automobile is considered to be bad by default and thus the air purifying unit 11 is controlled to purify the air at the first speed, i.e. the fan of the impeller 111 is controlled to operate at the first speed, and the scent dispenser 12 is controlled to dispense the first dispensing flow. In one example, the first dispensing flow may be set to be zero, which means the scent dispenser 12 is controlled to be closed and no scent is dispensed from the scent dispenser 12.

During the air purifying process, the air detector 13 continuously detects the purified air in the cabin and provides the output signal to the processor 14. The processor 14 receives the output signal from the air detector 13 and determines the quality of the purified air, based on the output signal. When the detected quality of the purified air is still higher than the first threshold, the processor 14 maintains the current operating speed of the air purifying unit 11 and the current dispensing flow of scent dispensed by the scent dispenser 12.

When the quality of the purified air becomes less than or equal to the first threshold, the processor 14 controls the air purifying unit 11 to purify air at the second speed and controls the scent dispenser 12 to dispense the second dispensing flow of scent. After that, when the air detector 13 detects that the quality of the purified air has become bad again, that is, the quality of the purified air exceeds the first threshold, the processor 14 controls the air purifying unit 11 to purify air at the first speed and controls the scent dispenser 12 to dispense the first dispensing flow.

Advantageously, the air treatment device 10 may further comprise a user interface (not shown), which may include one or more options indicative of different operations. For example, one option on the user interface may indicate 'starting the operation of removing odor smell', and another option on the user interface may indicate 'stopping the operation of removing odor smell'.

During the air purifying process, if the user perceives an unpleasant odor smell in the cabin of the automobile, then he/she may choose the option indicative of 'starting the operation of removing odor smell' on the user interface. In response to the user's choice, a first signal is generated to the processor 14. The processor 14, based on the first signal, controls the scent dispenser 12 to dispense a predefined dispensing flow and controls the air purifying unit 11 to purify air at a predefined speed. During the operation of removing odor, the processor 14 does not process the output signal from the air detector 12 any longer, that is to say, the air purifying unit 11 continues to operate at the predefined speed and the scent dispenser 12 continues to dispense the predefined dispensing flow of scent.

Advantageously, the predefined dispensing flow may be set to be the largest possible dispensing flow of the scent dispenser 12; the predefined speed may be set to be the highest speed at which the purifying unit 11 can operate. As a result, the odor can be removed within a very short period of time. It will be appreciated that, in practical usage, the predefined dispensing flow can be any flow larger than the current dispensing flow, and the predefined speed can be any speed higher than or equal to the current speed at which the air purifying unit 11 operates.

After that, if the user perceives that the odor has been removed, then he/she may choose the option indicative of 'stopping the operation of removing odor' on the user interface. In response to the user's choice, a second signal is generated to the processor 14. Based on the second signal, the processor 14 again receives or processes the output signal from the air detector 13, determines the quality of the purified air based on the output signal, and finds, from the mapping table, the desired operating speed of the air purifying unit 11 and the desired dispensing flow of scent corresponding to the determined quality of the purified air. Then, the processor 14 controls the air purifying unit 11 to purify air at the desired operating speed and controls the scent dispenser 12 to dispense the desired flow of scent.

Alternatively, the option indicative of 'stopping the operation of removing odor' on the user interface may be omitted. After the processor 14 has controlled the scent dispenser 12 to dispense a predefined dispensing flow of scent and has controlled the air purifying unit 11 to purify air at a predefined speed, based on the first signal, the processor 14 may start timing. When the predefined duration is reached, the processor 14 again receives or processes the output signal from the air detector 13, determines the quality of the purified air, based on the output signal, and finds, from the mapping table, the desired operating speed of the air purifying unit 11 and the desired dispensing flow of scent dispensed by the scent dispenser 12 corresponding to the determined quality of the purified air. Then, the processor 14 controls the air purifying unit 11 to purify air at the desired operating speed and controls the scent dispenser 12 to dispense the desired dispensing flow of scent.

In another aspect of the invention, a method of controlling a scent dispenser and an air purifying unit of an air treatment device is provided.

Figure 3:
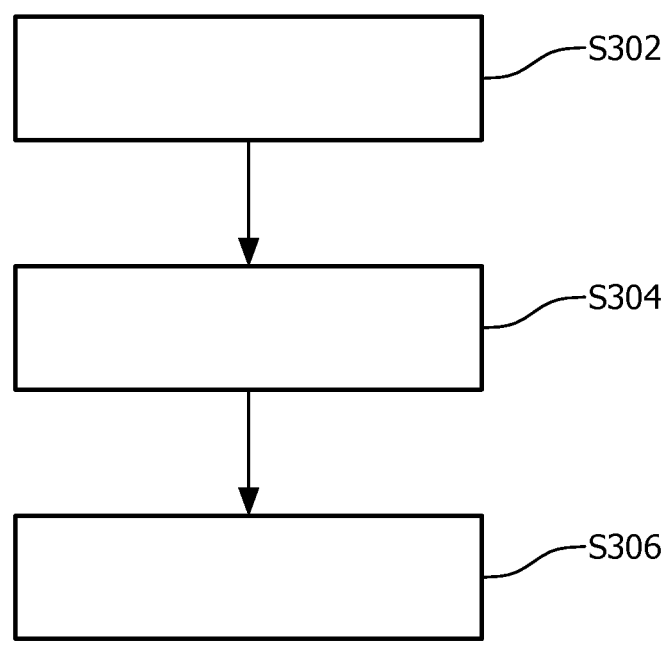
FIG. 3 depicts an exemplary embodiment of a flow chart of controlling a scent dispenser and an air purifying unit of an air treatment device according to another aspect of the invention.

FIG. 3 depicts an exemplary embodiment of a flow chart for controlling a scent dispenser and an air purifying unit of an air treatment device, wherein the air treatment device further includes an air detector and a processor.

Referring to FIG. 3, the method comprises a step S302 of purifying air by using the air purifying unit; a step S304 of detecting the purified air by using the air detector; and a step S306 of controlling, by using the processor, the operating speed of the air purifying unit and the dispensing flow of the scent dispensed by the scent dispenser, based on the detection result, wherein the dispensing flow of scent dispensed by the scent dispenser is decreased with the increase of the operating speed of the air purifying unit.

In one embodiment, the step S306 of controlling may further comprise the steps of determining the quality of the purified air based on the detection result; controlling the air purifying unit to purify air at a first speed and controlling the scent dispenser to dispense a first dispensing flow of scent when the quality of the purified air meets a first criterion; and controlling the air purifying unit to purify air at a second speed and controlling the scent dispenser to dispense a second dispensing flow when the quality of the purified air meets a second criterion, wherein the first speed is higher than the second speed and the first dispensing flow is smaller than the second dispensing flow.

Advantageously, the method may further comprise the steps of receiving a first signal, and in this manner, the step S306 of controlling may further comprise the step of controlling the scent dispenser to dispense a predefined dispensing flow, and controlling the air purifying unit to purify air at a predefined speed, based on the first signal, until a predetermined condition is satisfied.

Advantageously, the predetermined condition is satisfied if one of the following conditions is fulfilled:
a predefined duration is reached;
a second signal is received.

In a further aspect of the invention, there is provided a set of computer executable instructions configured to perform the steps S302 to S306 of FIG. 3.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the apparatus claims enumerating several units, several of these units can be embodied by one and the same item of hardware or software. The usage of the words first, second and third, et cetera, does not indicate any ordering. These words are to be interpreted as names.

The invention claimed is:

1. An air treatment device comprising:
an air purifying unit configured to purify:
a scent dispenser configured to dispense scent;
an air detector configured to detect the purified air and provide an output signal, wherein the air detector comprises a particle sensor;
a processor configured to:
receive the output signal from the air detector; and
control an operating speed of the air purifying unit and the dispensing flow of scent dispensed by the scent dispenser based on the output signal, wherein the dispensing flow of scent dispensed by the scent dispenser is decreased with an increase of the operating speed of the air purifying unit.

2. The air treatment device of claim 1, wherein the processor is configured to
determine a quality of the purified air based on the output signal;
control the air purifying unit to purify air at a first speed and control the scent dispenser to dispense a first dispensing flow of scent when the quality of the purified air meets a first criterion; and control the air purifying unit to purify air at a second speed and control the scent dispenser to dispense a second dispensing flow of scent when the quality of the purified air meets a second criterion, wherein the first speed is higher than the second speed and the first dispensing flow is smaller than the second dispensed flow.

3. The air treatment device of claim 2, further comprising a user interface configured to receive a first signal and provide the first signal to the processor;

wherein the processor is further configured to:
control the scent dispenser to dispense a predefined dispensing flow of scent and control the air purifying unit to purify air at a predefined speed, based on the first signal, until a predetermined condition is satisfied.

4. The air treatment device of claim 3, wherein the predetermined condition comprises one of:
whether a predefined duration has expired and
whether a second signal is received.

5. An air treatment device comprising:
a scent dispenser;
an air purifying unit
a particle sensor air detector; and
a processor:
detecting air purified by the air detector;
controlling an operating speed of the air purifying unit and a dispensing flow of the scent dispensed by the scent dispenser, based on a result of the detected purified air, wherein the dispensing flow of scent dispensed by the scent dispenser is decreased with an increase of the operating speed of the air purifying unit.

6. The device of claim 5, wherein the processor further:
determining a quality of the purified air based on the detection result;
controlling the air purifying unit to purify air at a first speed and controlling the scent dispenser to dispense a first dispensing flow of scent when the quality of the purified air meets a first criterion; and
controlling the air purifying unit to purify air at a second speed and controlling the scent dispenser to dispense a second dispensing flow of scent when the quality of the purified air meets a second criterion,
wherein the first speed is larger than the second speed and the first dispensing flow is smaller than the second dispensing flow.

7. The device claim 6, the processor further:
receiving a first signal; and
controlling the scent dispenser to dispense a predefined dispensing flow of scent and controlling the air purifying unit to purify air at a predefined speed, based on the first signal, until a predetermined condition is satisfied.

8. The device of claim 7, wherein the predetermined condition is satisfied if one of is fulfilled:
a predefined duration is reached; and
a second signal is received.

9. A set of computer-executable instructions stored on a non-transitory medium, which is not a signal or a wave, which when accessed by a processor causes the processor to:
control:
an operating speed of an air purifying unit, and
a dispensing flow of a scent dispensed by a scent dispenser, based on a detection result provided by a particle sensor detection system, wherein the dispensing flow of scent dispensed by the scent dispenser is decreased with an increase of the operating speed of the air purifying unit.

* * * * *